United States Patent
Engel et al.

(10) Patent No.: US 8,500,688 B2
(45) Date of Patent: Aug. 6, 2013

(54) RETROGRADE CORONARY SINUS PERFUSION CANNULA AND METHODS OF USING SAME

(75) Inventors: Rebecca L. Engel, Kalamazoo, MI (US); David E. Weston, Minneapolis, MN (US); Robert J. Lawrence, Grand Rapids, MI (US); Ernest Rodriguez, Rockford, MI (US); Donald R. Sandmore, Lyons, CO (US); Teresa A. Teunis, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 616 days.

(21) Appl. No.: 12/424,798

(22) Filed: Apr. 16, 2009

(65) Prior Publication Data

US 2010/0268159 A1 Oct. 21, 2010

(51) Int. Cl.
*A61M 31/00* (2006.01)

(52) U.S. Cl.
USPC .................................................. 604/103.08

(58) Field of Classification Search
USPC ............. 604/117, 93.01, 95.01, 96.01, 95.02, 604/99.01, 103.06, 103.08, 97.01, 103.1, 604/99.03
See application file for complete search history.

(56) References Cited

U.S. PATENT DOCUMENTS

| | | |
|---|---|---|
| 3,351,463 A | 11/1967 | Rosner et al. |
| 3,848,605 A * | 11/1974 | Harautuneian et al. .. 128/207.15 |
| 4,516,970 A | 5/1985 | Kaufman et al. |
| 4,641,654 A | 2/1987 | Samson et al. |
| 4,665,906 A | 5/1987 | Jervis |
| 4,869,259 A | 9/1989 | Elkins |
| 4,977,897 A | 12/1990 | Hurwitz |
| 4,990,138 A | 2/1991 | Bacich et al. |
| 5,021,045 A | 6/1991 | Buckberg et al. |
| 5,024,668 A | 6/1991 | Peters et al. |
| 5,067,957 A | 11/1991 | Jervis |
| 5,081,997 A | 1/1992 | Bosley et al. |
| 5,197,952 A | 3/1993 | Marcadis et al. |
| D335,705 S | 5/1993 | Buckberg et al. |
| 5,226,427 A | 7/1993 | Buckberg et al. |
| 5,230,348 A | 7/1993 | Ishibe et al. |
| 5,231,989 A | 8/1993 | Middleman et al. |
| 5,290,231 A | 3/1994 | Marcadis et al. |
| 5,344,399 A | 9/1994 | DeVries |
| 5,345,937 A | 9/1994 | Middleman et al. |
| 5,385,548 A | 1/1995 | Williams et al. |
| 5,395,330 A | 3/1995 | Marcadis et al. |
| 5,401,244 A | 3/1995 | Boykin et al. |
| 5,411,476 A | 5/1995 | Abrams et al. |
| 5,423,745 A | 6/1995 | Todd et al. |
| 5,443,448 A | 8/1995 | DeVries |
| 5,556,844 A | 9/1996 | Reichert et al. |
| 5,558,644 A | 9/1996 | Boyd et al. |
| 5,597,378 A | 1/1997 | Jervis |
| 5,637,089 A * | 6/1997 | Abrams et al. ............. 604/95.01 |
| 5,738,652 A | 4/1998 | Boyd et al. |
| 5,759,154 A | 6/1998 | Hoyns |
| 5,769,812 A | 6/1998 | Stevens et al. |
| 5,846,199 A | 12/1998 | Hijlkema et al. |
| 5,863,366 A | 1/1999 | Snow |
| 5,882,346 A | 3/1999 | Pomeranz et al. |
| 5,885,238 A | 3/1999 | Stevens et al. |

(Continued)

*Primary Examiner* — Nicholas Lucchesi
*Assistant Examiner* — Pritesh Patel (57) ABSTRACT

A retrograde coronary sinus perfusion catheter including a tubular catheter body having a proximal end, a distal end, and an inner lumen, and an inflatable balloon spaced proximally from the distal end of the catheter body, wherein the balloon is echogenically enhanced.

14 Claims, 8 Drawing Sheets

U.S. PATENT DOCUMENTS

| | | | |
|---|---|---|---|
| 5,913,842 A | 6/1999 | Boyd et al. | |
| 5,941,857 A * | 8/1999 | Nguyen et al. | 604/263 |
| 5,944,700 A * | 8/1999 | Nguyen et al. | 604/263 |
| 5,948,489 A | 9/1999 | Hopkins | |
| 5,967,988 A | 10/1999 | Briscoe et al. | |
| 5,993,424 A | 11/1999 | Lorenzo et al. | |
| 5,997,509 A * | 12/1999 | Rosengart et al. | 604/164.01 |
| 6,165,292 A | 12/2000 | Abrams et al. | |
| 6,280,539 B1 | 8/2001 | Abrams et al. | |
| 6,461,453 B1 | 10/2002 | Abrams et al. | |
| 6,517,516 B1 * | 2/2003 | Caizza | 604/110 |
| 6,540,721 B1 | 4/2003 | Voyles et al. | |
| 6,569,114 B2 * | 5/2003 | Ponzi et al. | 604/95.04 |
| 6,638,372 B1 | 10/2003 | Abrams et al. | |
| 6,682,608 B2 | 1/2004 | Abrams et al. | |
| 6,962,588 B2 * | 11/2005 | Sauvageau et al. | 606/41 |
| 7,244,317 B2 | 7/2007 | Gaur | |
| 2008/0045900 A1 * | 2/2008 | Alchas et al. | 604/117 |
| 2008/0154136 A1 | 6/2008 | Webler | |

* cited by examiner

RETROGRADE CORONARY SINUS PERFUSION CANNULA AND METHODS OF USING SAME

TECHNICAL FIELD

The present invention relates to a cannula and introducer system. More particularly, it relates to a cannula and introducer that can be placed into the coronary sinus via transatrial insertion using a thoracotomy or mini-sternotomy surgical technique.

BACKGROUND

When performing surgical procedures on the heart, it can be advantageous and/or necessary to interrupt the normal operation of the heart. In fact, it is often necessary for cardiac surgery to use cardiopulmonary-bypass techniques and to isolate the heart from its source of blood supply. One technique for preparing the heart for surgery in this way is to infuse cold cardioplegic fluid to cool and stop the beating of the heart. Cardioplegia can be administered in an antegrade manner (i.e., through the arteries and in the normal direction of blood flow), in a retrograde manner (i.e., through the veins in the opposite direction of normal blood flow) or in a combination of antegrade and retrograde manners. Due to some of the risks and inconveniences of antegrade cardioplegia, particularly for aortic valve replacement, many surgeons prefer to utilize the techniques of retrograde cardioplegia.

Typically, retrograde cardioplegia is administered by inserting a balloon catheter into the coronary sinus area, inflating the balloon to stop the normal flow of blood into the right atrium, and perfusing the cardioplegic solution through the coronary veins in the opposite direction of blood flow. In order to insert the balloon catheter into the coronary sinus area, both the superior and inferior venae cavae must be tied and each must be cannulated, thereby isolating the right heart. The right atrium may then be opened without allowing the dangerous introduction of air into the circulatory system. Once the right atrium is open, the catheter can be inserted into the coronary sinus under direct visualization while the cardioplegic solution is administered. After this occurs, the right atrium can then be closed. This sequence of steps can be performed for each administration of cardioplegic fluid during a particular surgical procedure.

In order to have access to the heart for this direct visual placement of a catheter, many commonly used delivery methods require the creation of a large incision in the chest cavity to expose the heart. However, techniques have recently been developed to place these devices in the coronary sinus area in a more minimally invasive manner in order to lessen the trauma to the patient and the risks associated with relatively large incisions. Because direct visualization is not possible through the incision site when using these less-invasive types of surgery, other devices and methods have been developed to detect and monitor the placement of the catheter within the body. For example, a portion of a catheter can be echogenically enhanced so that it can be ultrasonically imaged and guided to the desired location in the heart of the patient, such as is described in U.S. Pat. No. 5,967,988 (Briscoe, et al.), which is commonly owned by the assignee of the present invention. One technique that can be utilized for such imaging involves transesophageal echocardiography (TEE), which can often provide the information necessary for proper navigation and location of the catheter. In other cases, however, the available TEE devices and methods do not provide sufficient information due to situations such as the use of devices that become undetectable when using 2-dimensional images of the TEE probe. Thus, there is continued desire to provide improved devices and methods for accurately and reliably visualizing remotely placed devices, such as portions of a retrograde cardioplegia cannula. It is further desirable to provide a trans-thoracic retrograde coronary sinus perfusion cardioplegia cannula that is visible using trans-esophageal echocardiography and fluoroscopy.

SUMMARY

Typically, retrograde cardioplegia cannulae are inserted through a full sternotomy incision into the coronary sinus under direct visualization. However, the devices of invention include retrograde cardioplegia cannulae that are visible under transesophageal echocardiography and fluoroscopy and that are deflectable for remote placement into the coronary sinus. The devices and methods of the invention are applicable to small incision approaches or direct visualization approaches, including thoracotomy and mini-sternotomy (port or right) approaches. The devices are used to perfuse cardioplegia in a retrograde approach.

In one aspect of the invention, a cannula is provided with a balloon adjacent to its distal end that is echogenically enhanced, such as with embedded glass microspheres and/or density-laden tungsten to improve the visibility of the three-dimensional balloon using transesophageal echocardiography techniques. This enables clear imagery and guidance along a fluid-filled path to various cardiac structures regardless of the intersection with the TEE probe, which is particularly advantageous when attempting to view a remotely placed device, such as when the cannula is a retrograde cardioplegia cannula One embodiment of a system of the invention includes a cannula having a balloon adjacent to its distal end with a manually inflatable balloon. An introducer of this system can include forward or backward tip deflection and can have marker bands near the tip. The system thus includes a retrograde coronary sinus perfusion cannula comprising a pressure monitoring line, a manually inflatable balloon, and deflectable introducer. Another embodiment of the invention includes a system with a retrograde coronary sinus perfusion cannula comprising an automatically inflatable balloon, which may include marker bands under the balloon. The balloon may include embedded glass microspheres. The introducer can again include forward or backward tip deflection.

In another aspect of the invention, a distally located silicone balloon of a catheter is attached to a catheter body that is not made of silicone using a technique that includes a balloon having apertures or slits at one or both of its ends. A tube made of the same material as the catheter is placed over the apertures and/or slits of the balloon and heated to force the material of the tube to flow through the apertures and/or slits to bond with the material of the catheter body. This technique of sandwiching a balloon made of a first material between two tubes made of a second material that is the same as or different from the first material can also advantageously be used with balloons that are made of other materials than silicone in that this technique can be advantageous for the bonding of tubular components that normally will not bond to each other.

In another aspect of the invention, a cannula introducer is provided with enhanced tip deflectability to aid in the placement of a cannula such as a retrograde coronary sinus perfusion cannula. The introducer is removable from the cannula body after the cannula is properly positioned within the patient. The introducer includes a malleable section to provide gross shapeability and stiffness to the cannula body and a deployable section to provide additional deflection of the cannula tip section for fine guidance into the coronary sinus. The user can control the amount of tip deflection and orientation with such an introducer.

In yet another aspect of the invention, a multi-lumen tube is provided that houses a continuous wire that is configured to engage with a fixed stop in one or more directions when tension is placed on the wire. The wire may include a number of configurations for engaging with the stop, such as a knot or a ball located along the wire. The fixed stop may be molded into a cap to be secured onto the end of a tube, for example, so that the wire is threaded through the cap for interaction with the stop.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Referring now to the Figures, wherein the components are labeled with like numerals throughout the several Figures, and initially to FIGS. 1-5, an embodiment of a catheter 10 in accordance with the invention is illustrated. In one aspect of the invention, catheter 10 may be referred to as an auto-inflate minimally invasive retrograde coronary sinus perfusion cannula. The catheter 10 generally includes a catheter body 12 having a distal end 14 and a proximal end 16. The catheter 10 further includes a balloon 18 attached to the catheter body 12 and spaced proximally from the distal end 14. The catheter 10 can further include an optional suture ring 22 that can be used in the process of securing the catheter 10 to a location within the patient.

Figures 1, 2:
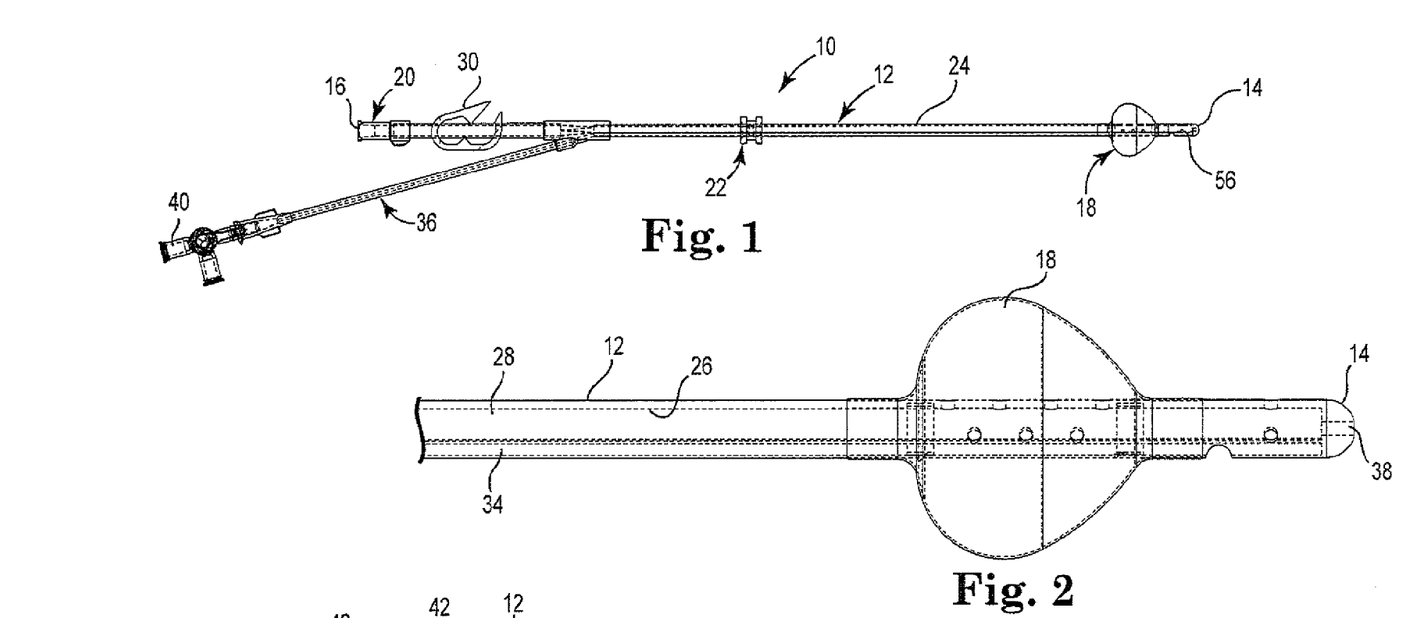
FIG. 1 is a front view of one embodiment of a catheter of the present invention.
FIG. 2 is an enlarged view of a tip portion and balloon of the catheter of FIG. 1.
Figure 3:
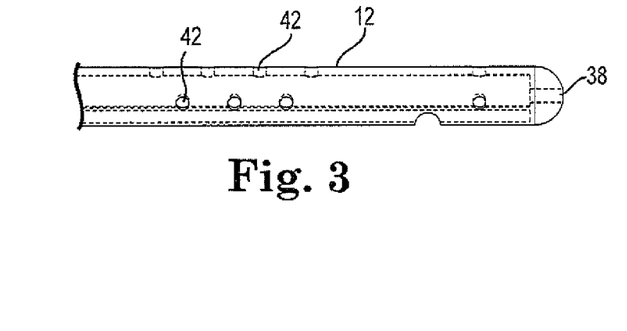
FIG. 3 is an enlarged view of a tip portion of the catheter body of FIG. 1.
Figure 4:
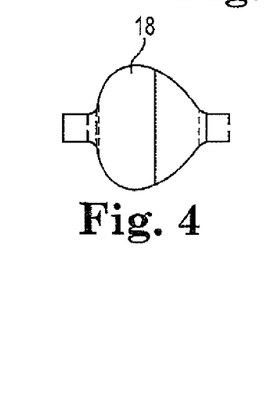
FIG. 4 is a side view of the balloon of FIG. 1.
Figure 5:
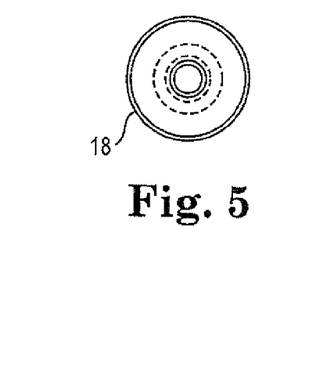
FIG. 5 is a cross-sectional side view of the balloon of FIG. 4.

The catheter body 12 is preferably formed from a flexible material that allows for introduction and placement within the body of a patient. The catheter body may be made of materials such as silicone or other biocompatible materials or combinations of materials and may be a dual lumen tube, for example. The catheter body 12 is generally tubular in cross section and includes an outer surface 24 and an inner surface 26 within the interior of the body 12. The infusion lumen 28 defines an interior infusion lumen 28 through which fluids can flow. The inner surface 26 extends to an aperture 38 at the distal end 14 of the catheter body 12 so that fluid can flow from this aperture 38 to the desired location in the patient. The catheter 10 may further include a locking female luer 20 or other device or apparatus for connecting the catheter 10 to a source of cardioplegic fluid. The catheter 10 is further provided with a clamping member or pinch clamp 30 mounted on the catheter body adjacent to the proximal end 16, which can be used to aid in controlling fluid flow. The clamping member 30 is reconfigurable and can be manipulated to squeeze the catheter body 12 to limit or stop the flow of fluid. The clamping member 30 may be configured so that it will "lock" in a closed position that will stop the flow of fluid through the catheter body 12 until the clamping member 30 is subsequently unlocked to again allow the flow of fluid.

The catheter 10 may further be provided with a separate pressure monitoring lumen 34 that extends generally from the distal end 14 of the catheter body 12 proximally along the length of the catheter body 12. This pressure monitoring lumen 34 may be provided as a tube that is positioned within the interior infusion lumen, or may instead be integrally molded into the catheter body 12. In this embodiment, a pressure monitoring line 36 extends from a proximal end of the pressure monitoring lumen 34. A proximal end of the pressure monitoring line 36 can further be provided with one or more locking luers 40 or other devices for connection to a pressure-monitoring device. In this way, the pressure-monitoring device can be in fluid communication with the inside of the body organ in which the catheter 10 is positioned in order to monitor the fluid pressure within that organ.

In some embodiments of the invention, the catheter may be provided with a balloon that needs to be inflated via a separate inflation lumen. The balloon 18 of the catheter 10, however, is considered to be automatically inflatable in that it does not require a separate lumen for inflation. Rather, the balloon 18 is compressible, such as with a sheath or other compression device, during the insertion of the catheter 10 into the patient, then expandable back to its inflated or expanded condition upon removal of the external device, such as the sheath. In this embodiment, the catheter body 12 is further provided with at least one, and preferably several, apertures 42 that are positioned between the ends of the balloon 18 so that they are generally located within the central portion of the balloon. These apertures 42 are in communication with the interior infusion lumen 28 of the catheter body 12.

The balloon 18 is preferably sufficiently flexible to be folded or compressed relatively flat against the body of the cannula or catheter. In addition, the balloon is preferably capable of obstructing and measuring pressure in the coronary sinus and must also be able to be inserted in the coronary sinus. In an exemplary embodiment, the maximum insertion and removal force of the balloon into the coronary sinus is less than about 1.0 pounds, although the force can be greater than about 1.0 pounds. In an exemplary embodiment, the body of the catheter should have at least one hole for balloon inflation, where this hole can have an inner diameter of approximately 0.076 inches, although it can be smaller or larger than this size, depending on the desired inflation parameters. In an exemplary embodiment, the balloon can also have some or all of the following characteristics: (1) have a minimum outer diameter when fully inflated that is equal to or greater than 0.590 inches, where the minimum outer diameter can be based on the coronary sinus diameter at 10 mm proximal to the ostium; (2) be capable of withstanding approximately 1.93 psi (100 mm Hg) of internal pressure without material or seal failure; (3) have a maximum balloon durometer of approximately 80 A; (4) have a maximum deflection force at 0.125 inches travel of less than or equal to 0.5 pounds, where the deflection force that causes the balloon to fold against the cannula body is preferably less than or equal to the tracking force inside the vessel; and (5) have a minimum balloon joint strength of greater than or equal to approximately 1.0 pounds, using axial pull and peel testing procedures.

The catheter 10 optionally includes at least one auxiliary discharge aperture 56 at the distal end 14 of the catheter body 12. The discharge aperture 56 is located distally from the balloon 18 and can extend from the interior of the infusion lumen 28 radially through the thickness of the catheter body 12. In this way, should the distal end 14 of the catheter body 12 become blocked or occluded, the auxiliary discharge aperture(s) 56 can allow the cardioplegic fluid to exit from the catheter and into the desired coronary sinus or other body organ.

As set out above, the balloon 18 is attached to the catheter body 12, and more particularly, the balloon 18 is attached to the outer surface 24 of the catheter body. The balloon 18 can be made of a variety of materials, such as silicone, latex, polyurethane, or PVC, for example, and the catheter body 12 can likewise be made of a variety of materials, such as silicone or non-silicone materials like PVC, Pebax or elasthane.

Figure 6:
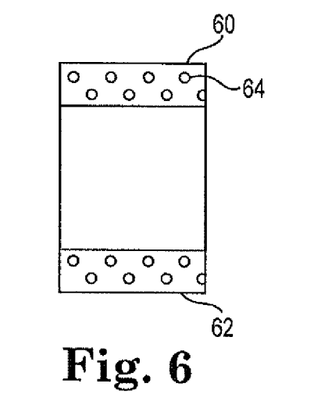
FIG. 6 is a front view of one embodiment of a balloon of the present invention, including a series of apertures at its proximal and distal ends.
Figure 7:
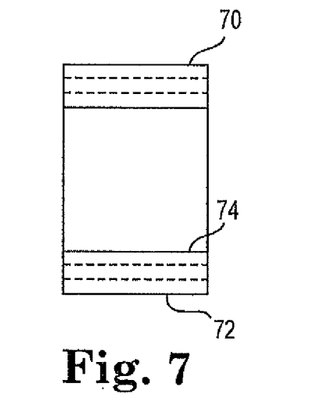
FIG. 7 is a front view of another embodiment of a balloon of the invention, including a series of slits at its proximal and distal ends.

In one exemplary embodiment of the invention, the balloon is made of silicone to take advantage of the fact that silicone is expandable and relatively conformable to the shape of the vessel in which it is inserted, which can provide for excellent occlusion of a desired vessel or passageway. In this same embodiment, the catheter body is made of a non-silicone material, which can provide certain challenges for attachment of the balloon 18 to the catheter body 12. However, in order to attach the balloon 18 to the catheter body 12, the balloon 18 of this embodiment is provided with a relatively circular or tubular cross-section having multiple holes or slits near both its proximal and distal end portions, as is illustrated in FIGS. 6 and 7. With reference to FIG. 6, a proximal end 60 and distal end 62 of the balloon are each provided with two rows of apertures or holes 64 that are staggered relative to each other. With reference to FIG. 7, a proximal end 70 and distal end 72 of the balloon are each provided with two rows of elongated slits 74 that can be aligned or staggered relative to each other around the circumference of the balloon.

Figure 8:
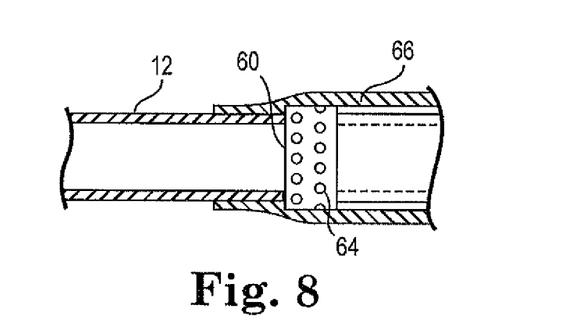
FIG. 8 is a partial cross-sectional side view of the balloon of FIG. 6 secured to a catheter body.
Figure 9:
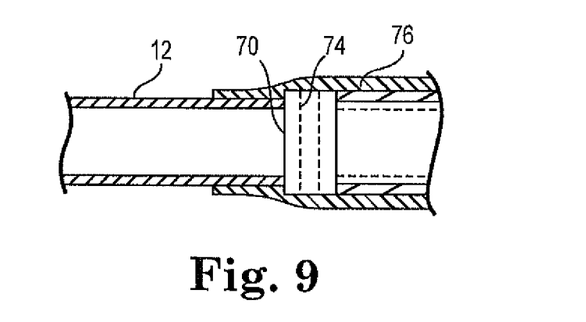
FIG. 9 is a partial cross-sectional side view of the balloon of FIG. 7 secured to a catheter body.

In order to attach the balloon 18 to the catheter body 12, the silicone balloon 18 is slid over the catheter body 12 to its desired location relative to the length of the body 12, as is illustrated in FIGS. 8 and 9. In FIG. 8, an outer tube 66, which is made of the same material as the catheter body 12 or a material that is bondable to the catheter body 12, is then positioned over the proximal end 60 of the balloon. The outer tube 66 is then heated to a temperature that allows it to flow through the holes 64 until it contacts and bonds with the material of the outer tube 66. This process may be referred to as "balloon reflow" or "reflow". The same process may be used for attaching the distal end 62 of the balloon to the catheter body 12. Similarly, FIG. 9 illustrates an outer tube 76, which is made of the same material as the catheter body 12 or a material that is bondable to the catheter body 12, positioned over the proximal end 70 of the balloon. The outer tube 76 is then heated to a temperature that allows it to flow through the slits 74 until it contacts and bonds with the material of the outer tube 76. The same process may be used for attaching the distal end 72 of the balloon to the catheter body 12.

In accordance with the invention, more or less than two rows of slits or apertures may be provided on either or both of the proximal and distal ends of the balloons. Further, each of the rows may contain slits, apertures, or combinations of slits, apertures, or other types of openings, and each row may have the same or different types of openings relative to any adjacent row or rows of openings. Again, the slits or apertures can be staggered or somewhat offset relative to the slits or apertures in adjacent rows; however, at least some of the slits and/or apertures may instead be aligned with each other in adjacent rows. In any case, the size, number, shape, and alignment of the slits and/or apertures should be designed and/or chosen so that an adequate amount of material of the outer tube can flow through them for contact and bonding with outer surface of a catheter body. In addition, the outer tube that is used for the process of reflowing should be adequately thick to provide sufficient strength to the bond between the outer tube and the catheter body to prevent or minimize the chances of detachment of the balloon from the catheter body during inflation of the balloon or other manipulation of the catheter However, the outer tube should not be so thick that it interferes with the other characteristics of the catheter relative to flexibility, strength, and the like.

Referring again to FIGS. 1-5, it is desirable that the location of the various portions of the catheter 10 can be detected as it is being positioned in the patient. In particular, the location of the distal end 14 and the adjacent balloon 18 is preferably viewable by the clinician to insure that it is properly located during the surgical procedure. One such detection method includes echogenically enhancing the balloon, such as a balloon that is made entirely or partially of polyurethane. The term "echogenicity" or "echogenic" refers to the relative extent that a surface reflects incident ultrasound wave energy directly back to a sensor, which is proximal to the source or emitter of the ultrasonic wave energy. Ultrasound energy from a transducer can reflect off of the echogenically-enhanced balloon and back to the transducer. In accordance with the invention, the material composition of the balloon 18 contains an echogenicity enhancement embedded within it to improve its visibility under transesophageal echocardiography (TEE). The embedded material may consist of hollow particles or other hollow material, such as glass microspheres. Alternatively, the embedded material may consist of a material having a significantly greater density as compared to the surrounding material, such as tungsten. In yet another alternative, the embedded material may consist of a material with a greatly roughened or jagged texture. In yet another embodiment, the embedded material may consist of a combination of hollow particles or materials, a material with a relatively high density, and/or a material with a roughened texture. Any or a combination of these material characteristics, when embedded in the wall of the balloon, can reflect ultrasonic waves and thereby display a bright image as shown on transesophageal echocardiography. In this way, the balloon will be capable of being accurately and quickly guided into a desired vessel or chamber of the body because a two-dimensional image is rendered regardless of its angle of intersection with that of the transesophageal echocardiography probe.

If the echogenicity enhancement is provided with hollow glass microspheres embedded within the balloon material, the microspheres are provided in such a way that there are sufficient density differences in the materials that are detectable using ultrasound. That is, the number, size, shape and other properties of the microspheres can be selected to achieve different material properties for the balloon, depending on the particular application. In addition, the microspheres should be chosen so that the performance of the balloon itself is not compromised. In one exemplary embodiment of the balloon, the balloon is made of polyurethane having a maximum durometer of 80 A, which can provide a balloon embedded with microspheres having durometer readings between about 70-72 A. The hollow microspheres can be provided in a range of about 38-90 micrometers. The minimum concentration of microspheres by weight of glass spheres to urethane solution can be about 0.00200:1 and the maximum concentration of microspheres can be about 0.00625:1. At the lower end of the range (0.00200:1 concentration of glass microspheres to urethane), the balloon can have durometer readings between about 67 A and 72 A, while at the upper end of the range (0.00625:1 concentration of glass microspheres to urethane), the balloon can have durometer readings between about 61 A and 67 A. In another exemplary embodiment of the balloon, the balloon is made of a silicone material, to which glass microspheres can be added. With silicone, the balloon would have a durometer that is considerably lower than that of a urethane balloon; however, silicone can be selected for certain applications in which such a lower durometer would be acceptable.

Figure 10:
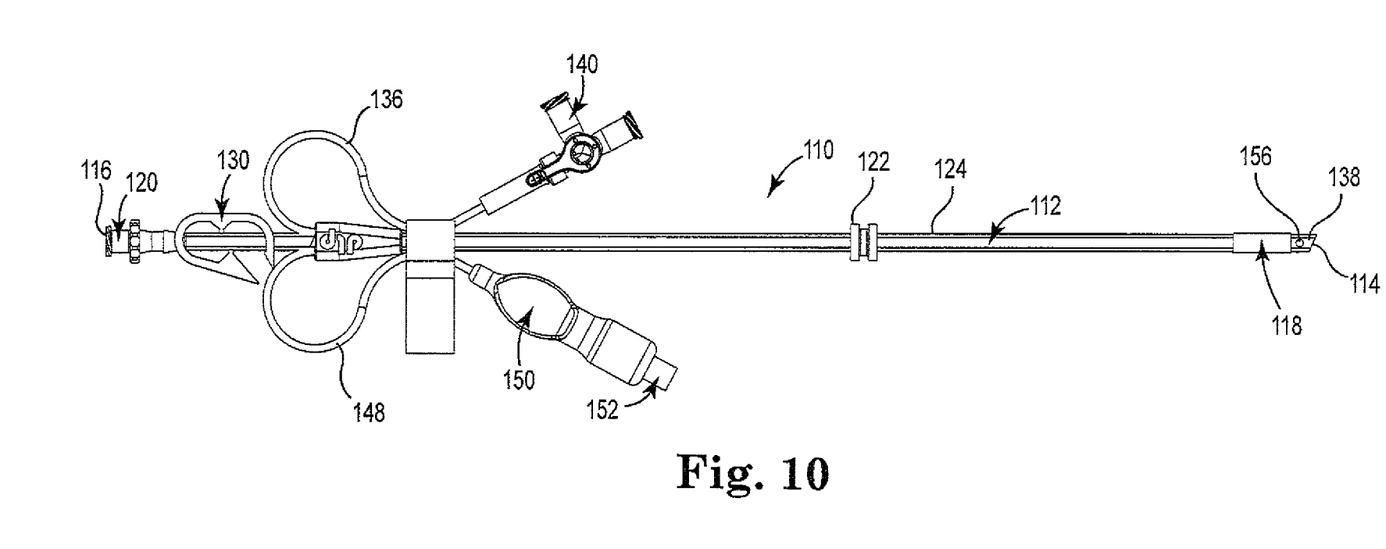
FIG. 10 is a side view of another embodiment of a catheter of the present invention.

FIG. 10 illustrates another embodiment of a catheter 110 in accordance with the invention. In one aspect of the invention, catheter 110 may be referred to as a manual-inflate minimally invasive retrograde coronary sinus perfusion cannula. The catheter 110 generally includes a catheter body 112 having a distal end 114 and a proximal end 116. The catheter 110 further includes a balloon 118 attached to the catheter body 112 and spaced proximally from the distal end 114. The catheter 110 can further include an optional suture ring 122 that can be used in the process of securing the catheter 110 to a location within the patient.

The catheter body 112 is preferably formed from a flexible material that allows for introduction and placement within the body of a patient. The catheter body may be made of materials such as silicone or other biocompatible materials or combinations of materials. The catheter body 112 is generally tubular in cross section and includes an outer surface 124 and an inner surface within the interior of the body 112. The infusion lumen defines an interior infusion lumen through which fluids can flow. The inner surface extends to an aperture 138 at the distal end 114 of the catheter body 112 so that fluid can flow from this aperture 138 to the desired location in the patient. The catheter 110 may further include a luer 120 or other device or apparatus at its proximal end 116 for connecting the catheter 110 to a source of cardioplegic fluid. In order to aid in controlling the fluid flow, the catheter 110 is further provided with a clamping member or pinch clamp 130 mounted on the catheter body adjacent to the proximal end 116. The clamping member 130 is reconfigurable and can be manipulated to squeeze the catheter body 112 to limit or stop the flow of fluid. The clamping member 130 may be configured so that it will "lock" in a closed position that will stop the flow of fluid through the catheter body 112 until the clamping member 130 is subsequently unlocked to again allow the flow of fluid.

The catheter 110 may further be provided with a separate pressure monitoring lumen that extends from the distal end 114 of the catheter body proximally along the length of the catheter body 112. This pressure monitoring lumen may be provided as a tube that is positioned within the interior infusion lumen, for example, or may instead be integrally molded into the catheter body 112. In this embodiment, a pressure monitoring line 136 extends from a proximal end of the pressure monitoring lumen. A proximal end of the pressure monitoring line 136 can further be provided with a locking luer 140 or other device for connection to a pressure-monitoring device. In this way, the pressure-monitoring device can be in fluid communication with the inside of the body organ in which the catheter 110 is positioned in order to monitor the fluid pressure within that organ.

The catheter 110 is further provided with a separate inflation lumen, which extends along substantially the entire length of the catheter body 112. The inflation lumen may be provided as a tube that is positioned within the interior infusion lumen, for example, or may instead be integrally molded into the catheter body 112. In this embodiment, a tubular inflation line 148 extends from a proximal end of the inflation lumen. A conventional pilot balloon 150 and a check valve 152 are mounted on the end of the inflation line 148. The distal end of the inflation lumen terminates inside the balloon 118 so that fluid or air may pass through the inflation lumen to fill the balloon 118 for its expansion to a desired size. The check valve 152 prevents the fluid or air from escaping the balloon 118 and can thereby keep the balloon 118 inflated until the valve 152 is manually released. The fluid or air can then exit the balloon 118 through the inflation lumen and past the one-way valve 152.

The catheter 110 optionally includes at least one auxiliary discharge aperture 156 adjacent to the distal end 114 of the catheter body 112. The discharge aperture 156 is located distally from the balloon 118 and can extend from the interior of the infusion lumen radially through the catheter body 112. In this way, should the aperture 138 at the distal end 114 of the catheter body 112 become blocked or occluded, the auxiliary discharge aperture(s) 156 can allow the cardioplegic fluid to exit from the catheter and into the desired coronary sinus or other body organ. The balloon 118 of this embodiment can also be attached to the outer surface 124 of the catheter body 112, and can include any of the features described above relative to balloon attachment to the catheter, echogenicity enhancements, and the like.

Figure 11:
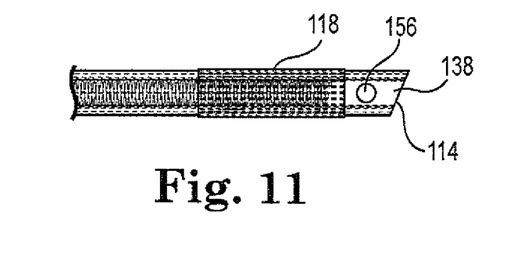
FIG. 11 is a cross-sectional side view of a tip portion of the catheter of FIG. 10.

FIG. 11 is an enlarged view of the tip area of the catheter 110, which shows portions of the structure with hidden lines. In particular, this figure illustrates a cannula or catheter body, which may be silicone, for example, with a spring coil embedded in the body wall. The spring coil is provided for kink resistance; however a different or additional structure from this spring coil may be provided to accomplish the function of kink resistance. The inside surface of the balloon 118 further is illustrated as having a series of longitudinal ribs, which are optional structures. The body of this catheter comprises three lumens, including a main fluid delivery lumen and two side lumens that are connected to tubes 136 and 148. The lumen to which tube 148 is attached is preferably closed or plugged at the distal end of the catheter and open beneath the balloon 118. The balloon 118 can be inflated using a syringe through the check valve 152.

The catheters of the present invention, along with catheters having at least some similar characteristics, can be placed in a desired location in a patient with the use of an introducer system. An introducer system can be temporarily inserted into a tubular opening, such as an infusion lumen, that extends along the length of the catheter or cannula. In accordance with the invention, a trans-thoracic retrograde coronary sinus perfusion device is provided that is maneuverable into the coronary sinus area of a patient through mini-sternotomy and right thoracotomy access points. In one aspect of the invention, the introducer system is provided with a malleable tip portion or section that provides gross shapeability and stiffness to the cannula body. The introducer system is further provided with a deployable section to provide additional deflection of the cannula tip section for fine guidance into the coronary sinus. The amount of tip deflection and orientation relative to the malleable shape can be controlled by the user. This capability of the system may be particularly advantageous when using surgical approaches in which the visibility of the heart and coronary sinus area are relatively limited.

Figure 12:
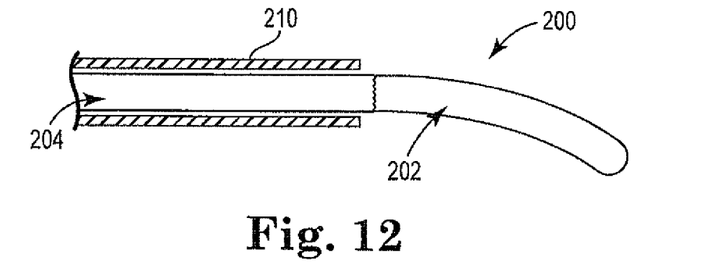
FIG. 12 is a partial cross-sectional side view of a tip portion of a steerable introducer in a deployed condition relative to a retractable sheath.
Figure 13:
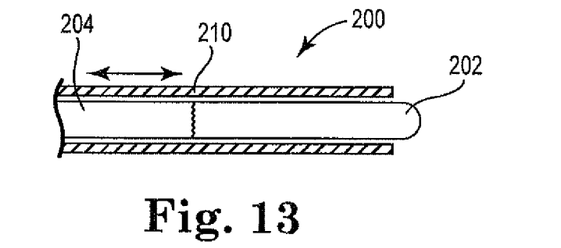
FIG. 13 is another side view of the tip portion of FIG. 12, with the introducer in a retracted or partially retracted condition relative to the retractable sheath.

Referring now to FIGS. 12 and 13, one embodiment of a distal end of an introducer 200 is illustrated. Introducer 200 includes a tip section 202 that is formed of a shape memory type of material, such as Nitinol, and a malleable stylet portion 204 that is adjacent and proximal to the tip section 202. FIG. 12 illustrates this end portion of introducer 200 in a deployed or partially deployed position relative to a retractable sheath 210, and FIG. 13 illustrates the end portion of the introducer 200 in a retracted or partially retracted position relative to the retractable sheath 210. In FIG. 13, the shape memory material of the tip section 202 has been straightened due to the constraints of the walls of the retractable sheath 210. The malleable portion 204 allows the user to define a portion of the shape, while the tip area 202 is provided with a preformed arc or bend that can be moved within the introducer body to either deploy or retract the shaped section. Once deployed, the direction of the tip section 202 can be changed by rotating the shape memory wire within the introducer body.

Figure 14:
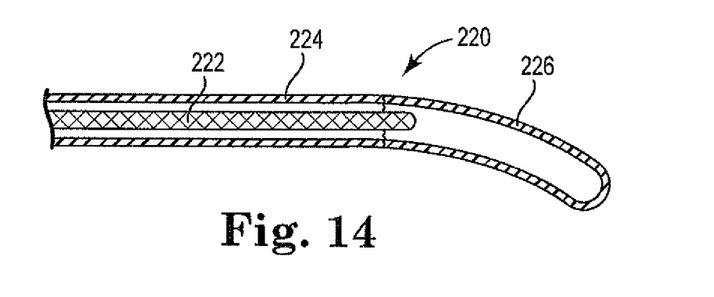
FIG. 14 is a cross-sectional side view of another tip portion of a steerable introducer.
Figure 15:
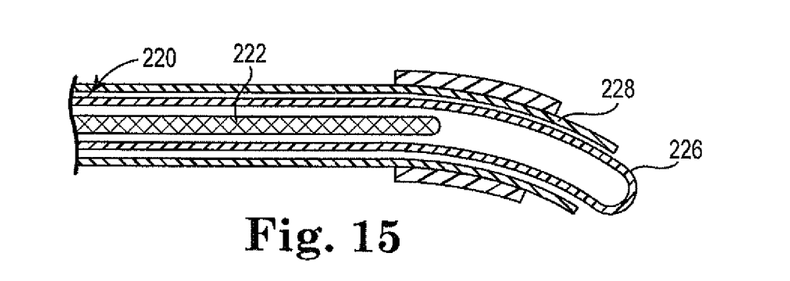
FIG. 15 is a cross-sectional side view of the tip portion of the introducer of FIG. 14 positioned relative to a cannula body.

FIGS. 14 and 15 illustrate another exemplary embodiment of a distal end of an introducer 220. Introducer 220 includes a retractable rod 222 that is positioned within a malleable tube 224 that has a tip portion 226. The retractable rod 222 may be made of a shape memory material, such as Nitinol, and the tip portion 226 may be made of a polymer material, for example. The retractable rod 222 is shown in FIG. 15 as positioned within a distal end portion of a cannula 228, which may be a retrograde coronary sinus perfusion cannula, for example. Deploying the shape memory material within the cannula body can deflect the tip of the cannula 228.

FIGS. 16-21 illustrate one embodiment of an introducer 300 in accordance with the invention. Introducer 300 generally includes a flexible spring tip 302 (e.g., comprising a drive wire made of a shape memory material, such as Nitinol), a malleable shaft 304, a luer taper 306, a grip 308, which may comprise a silicone material, and a handle 310 including a slider cap 312. In this illustrated version of the introducer 300, the spring tip 302 will be bent downwardly relative to the handle 310 when the slider cap 312 is slid toward a distal end 320 of the introducer 300. In another version of the introducer (not shown), the spring tip will be bent upwardly relative to the handle when the slider cap is slid toward the distal end of the introducer. In both of these versions, the spring tip will be relatively straight when the slider cap is positioned toward a proximal end 322 of the introducer 300. When the spring tip 302 is bent either downwardly or upwardly (i.e., the slider lever 312 is in its distal-most position), the spring tip 302 also can deflect side to side, such as with rotation of the slider lever 312 clockwise and counterclockwise relative to the handle 310. The desired deflection performance of the introducer 300 can be measured by its sweep angle, rotation, actuation, and the like.

Figure 16:
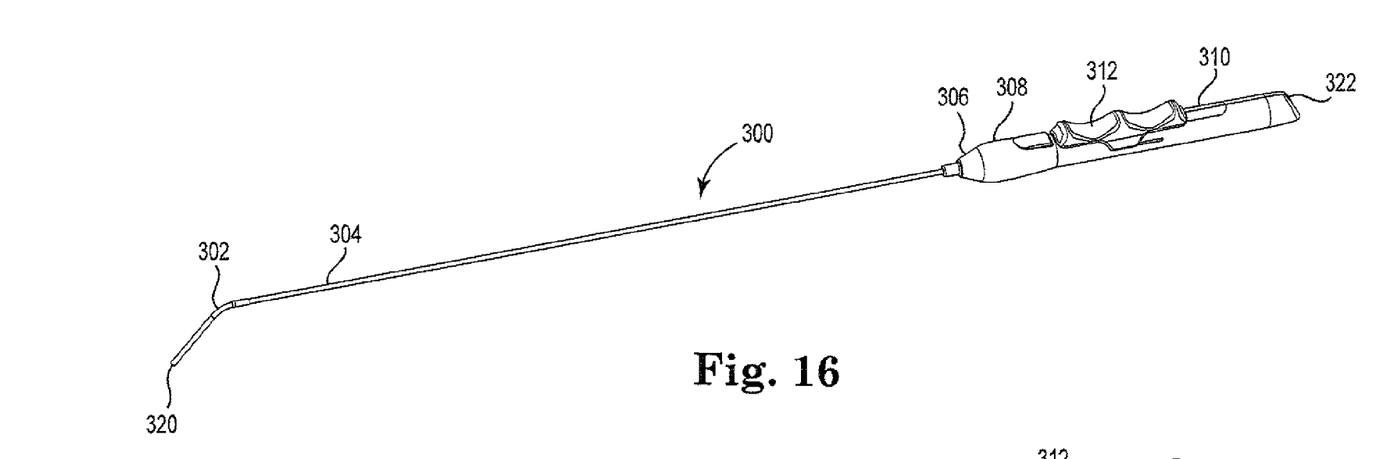
FIG. 16 is a perspective view of an embodiment of an introducer, in accordance with the invention.
Figure 17:
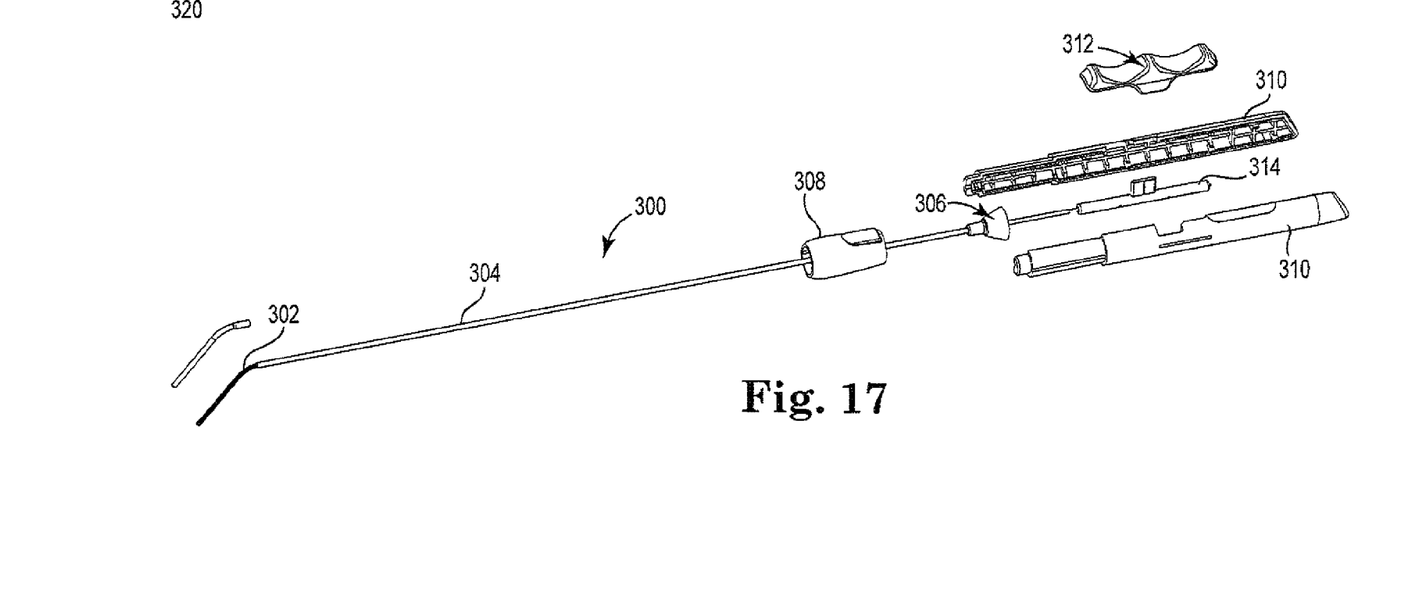
FIG. 17 is an exploded view of the introducer of FIG. 16.
Figure 18:
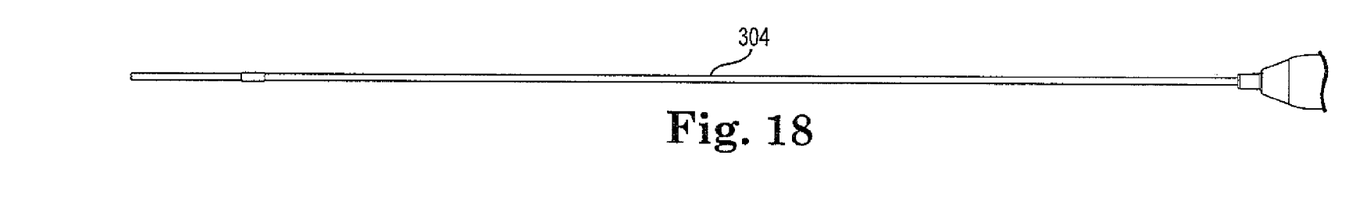
FIGS. 18-20 are side views of components of the introducer of FIGS. 16 and 17.
Figure 19:
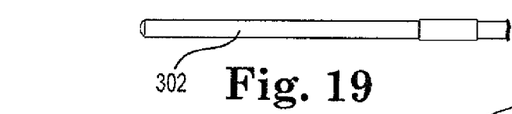
Figures 20, 21:
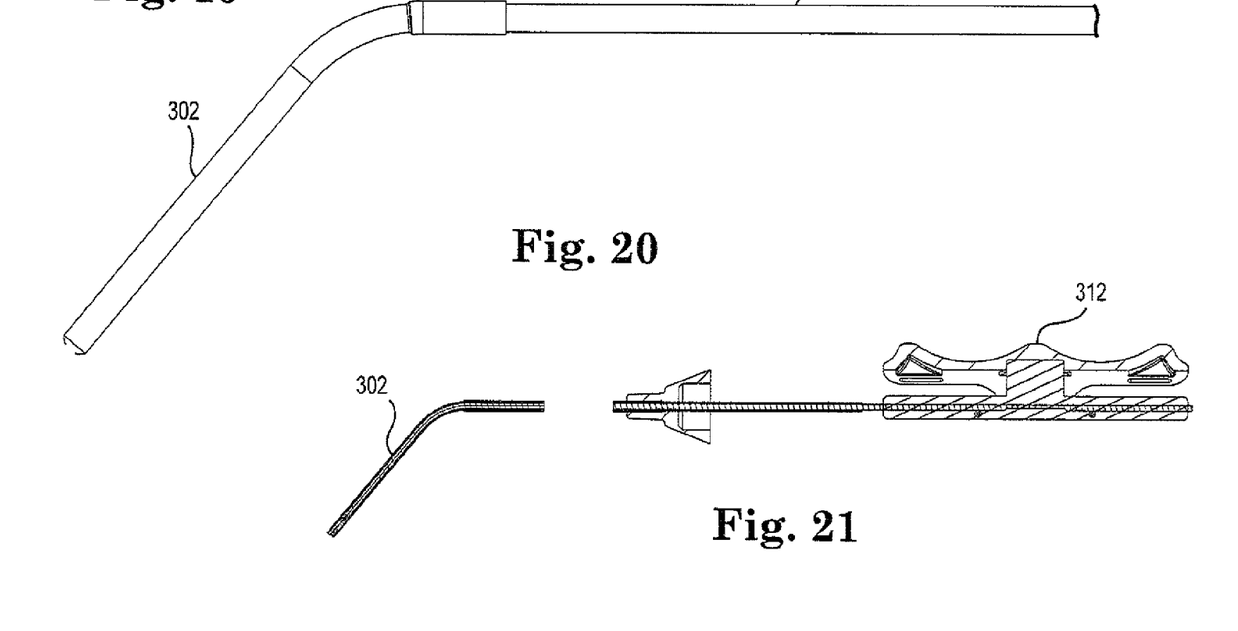
FIG. 21 is a cross sectional view of a portion of the introducer of FIG. 16.
Figure 22:
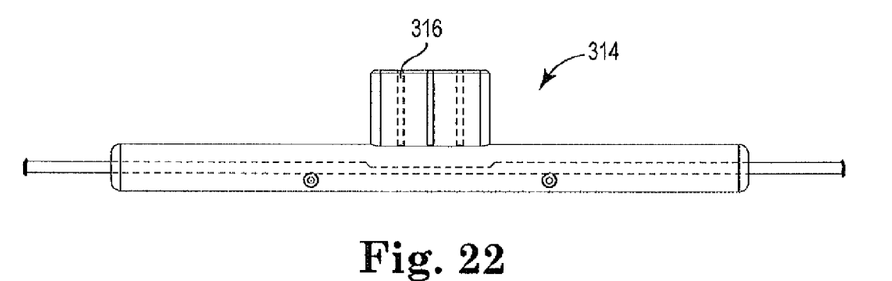
FIG. 22 is a side view of a lever mechanism of the introducer of FIG. 16.
Figure 23:
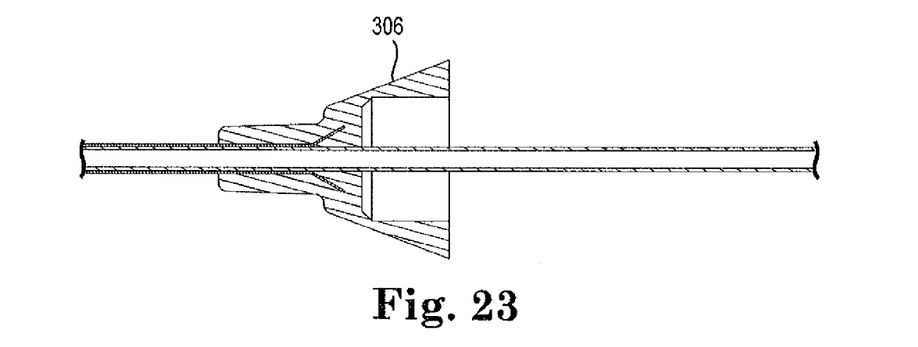
FIG. 23 is a cross-sectional view of a portion of the introducer of FIG. 16.
Figure 24:
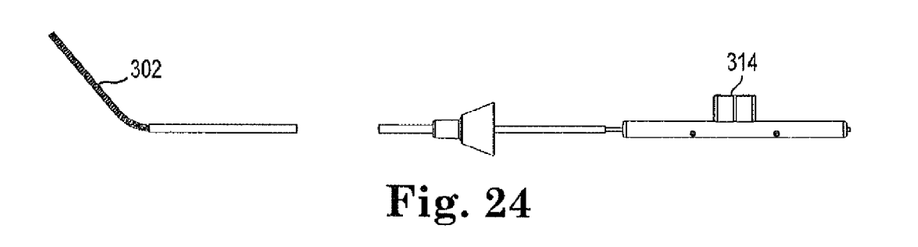
FIG. 24 is a side view of a sub-assembly of the introducer of FIG. 16.

In one exemplary embodiment of the introducer 300, the cannula tip is approximately 2 cm in length, and is controllable in vivo to be deflected to approximately 45 degrees and to be rotatable to approximately 40 degrees. Preferably, the tip deflection and tip rotation can be accomplished with one hand; such as can be accomplished with the slide lever 312 of this embodiment, which can be removably attached to the handle 310 via a lever connector 314. The lever connector 314 includes an extension 316 that is engageable with a corresponding aperture or slot in the bottom of the slider lever 312. The handle 310 is configured to allow the slider lever 312 to rotate clockwise and counterclockwise relative to the handle when the tip is in its bent configuration, but is also configured to prohibit any rotational movement of the slider lever relative to the handle when the tip is in its relatively straight configuration.

Figure 25:
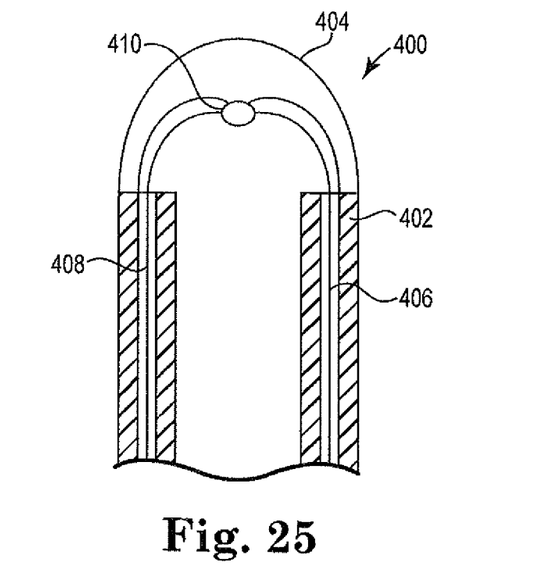
FIG. 25 is a cross-sectional side view of a distal portion of a catheter tube having steerability capabilities.
Figure 26:
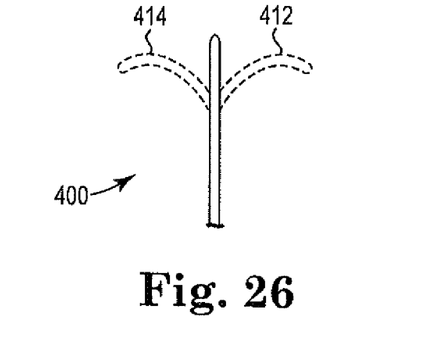
FIG. 26 is a side view of a distal portion of the catheter tube of FIG. 25, and schematically illustrating its deflection in two directions.

FIGS. 25 and 26 illustrate a distal end portion of multi-lumen tube assembly 400 that is deflectable in more than one direction. Tube assembly 400 includes a multi-lumen tube 402 through which wire sections 406 and 408 extend, where the wire sections 406, 408 can be portions of a continuous wire that extends to or through a stop structure 410. The tube assembly 400 further includes a cap portion 404. In order to provide for tip deflection in two directions (in one plane), tension is placed on one of the wire sections 406, 408, which engages the stop 410 and causes deflection of the tip. The wire sections can interact mechanically with the stop 410, or a continuous wire piece can include a knot or ball located along the wire that engages with a stop, for example. The stop may alternatively be molded into the cap that is secured onto the end of the tube, such that the wire is threaded through the cap for interaction with the stop. Pulling on the wire section 406 would then cause the tube assembly 400 to deflect in a first direction 412, and pulling on the wire section would cause the tube assembly 400 to deflect in a second direction 414, as is illustrated in FIG. 26.

In order to utilize the various aspects of the present invention, one exemplary process can include making a right thoracotomy incision and advancing a cannula and introducer into the right atrium and coronary sinus while the cannula and introducer are being visualized under transesophageal echocardiography (TEE). A TEE probe can be positioned in the esophagus or against the pericardium in the thoracic cavity, for example, for adequate visualization. TEE cine images can be captured of the four heart chambers and the coronary sinus and the trans-thoracic retrograde coronary sinus perfusion (TT-RCSP) device as it travels through the right atrium and into the coronary sinus using transesophageal echocardiography and/or fluoroscopy. Once proper positioning of the balloon is confirmed within the coronary sinus, the introducer will then be removed from the cannula.

An alternative process includes making a mini sternotomy incision and inserting a cannula and introducer through this and a right atriotomy incision. The cannula and introducer can be advanced into right atrium and coronary sinus, as visualized under TEE. For a manually inflating TT-RCSP device the balloon on cannula can be inflated to occlude the coronary sinus, with adequate occlusion being verified by ventricularization of pressure as observed via the pressure monitoring lumen in the cannula. TEE cine images can be captured of the four heart chambers and coronary sinus and the TT-RCSP device as it travels through the right atrium and into the coronary sinus. Once ventricularization of pressure is confirmed, the introducer will then be removed from the cannula.

Additional procedures described as aortic valve repair or replacement (AVR) and mitral valve repair or replacement (MVR) can be used to access the coronary sinus through a mini-sternotomy or right thoracotomy. The TT-RCSP cannula with introducer system can be passed through a chest incision and into the right atrium. The introducer, which can include a malleable body and additional tip deflection and rotation, as described above, is used to guide the cannula into the coronary sinus. Guidance of cannula and introducer within right atrium and into coronary sinus is facilitated using TEE. Once cannula is placed, cannula is secured using purse-string suture and the introducer can be removed.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A retrograde coronary sinus perfusion catheter comprising:
    a tubular catheter body having a proximal end, a distal end, and an inner lumen; and
    an inflatable balloon spaced proximally from the distal end of the catheter body, wherein the balloon is echogenically enhanced, wherein the balloon comprises a plurality of embedded hollow particles that provide the echogenic enhancement of the balloon.

2. The catheter of claim 1, wherein the hollow particles comprise glass microspheres.

3. The catheter of claim 1, wherein the balloon comprises a polyurethane material.

4. The catheter of claim 1, wherein the balloon is automatically expandable.

5. The catheter of claim 1, wherein the catheter body further comprises an inflation lumen having a distal end that terminates within an interior portion of the balloon, wherein a first end of a tubular inflation line extends from a proximal end of the inflation lumen, and wherein a balloon inflation device extends from a second end of the tubular inflation line.

6. The catheter of claim 5, wherein the balloon inflation device comprises a pilot balloon and a check valve that can be activated for inflation of the balloon.

7. A retrograde coronary sinus perfusion catheter comprising:
    a tubular catheter body having a proximal end, a distal end, and an inner lumen; and
    an inflatable balloon spaced proximally from the distal end of the catheter body, wherein the balloon is echogenically enhanced, wherein the echogenically enhanced balloon comprises density-laden tungsten.

8. A retrograde coronary sinus perfusion catheter system comprising:
    a tubular catheter body having a proximal end, a distal end, and an inner lumen;
    an inflatable balloon spaced proximally from the distal end of the catheter body, wherein the balloon is echogenically enhanced; and
    an introducer comprising a distal portion that is deflectable in at least one direction, and wherein the distal portion of the introducer is insertable into an infusion lumen that extends through at least a portion of a length of the tubular catheter body, wherein the introducer further comprises a retractable sheath having an interior area, wherein the malleable portion and distal portion of the introducer are at least partially positionable within the interior area of the sheath, and wherein at least the distal portion of the introducer is retractable and deployable relative to a distal end of the sheath.

9. The catheter of claim 8, wherein the introducer further comprises at least one marker band adjacent to the distal portion.

10. The catheter of claim 8, wherein the distal portion is formed of a shape memory material and wherein the introducer further comprises a malleable portion that is adjacent and proximal to the distal portion.

11. The catheter of claim 10, wherein the distal portion of the introducer comprises a flexible spring tip.

12. The catheter of claim 7, wherein the balloon is automatically expandable.

13. The catheter of claim 7, wherein the catheter body further comprises an inflation lumen having a distal end that terminates within an interior portion of the balloon, wherein a first end of a tubular inflation line extends from a proximal end of the inflation lumen, and wherein a balloon inflation device extends from a second end of the tubular inflation line.

14. The catheter of claim 10, wherein the balloon inflation device comprises a pilot balloon and a check valve that can be activated for inflation of the balloon.

* * * * *